United States Patent [19]

Diamond et al.

[11] 4,139,537

[45] Feb. 13, 1979

[54] 3-ARYLOXY-1-(2- OR 4-IMINODIHYDRO-1-PYRIDYL)-2-PROPANOL ANTIARRHYTHMIC COMPOUNDS

[75] Inventors: Julius Diamond; Ronald A. Wohl, both of Morris Plains, N.J.

[73] Assignee: Cooper Laboratories, Inc., Parsippany, N.J.

[21] Appl. No.: 701,028

[22] Filed: Jun. 29, 1976

[51] Int. Cl.$^2$ ............................................. C07D 213/16
[52] U.S. Cl. ................................. 546/309; 546/292; 546/297; 546/289; 546/305; 546/306; 546/308; 546/310; 546/311; 46/312; 424/256; 546/269; 546/274; 546/145; 546/177
[58] Field of Search ................... 260/296 B, 294.8 E, 260/294.9, 295 D, 295 AM; 424/256

[56] References Cited

U.S. PATENT DOCUMENTS

| | | | |
|---|---|---|---|
| 3,953,456 | 4/1976 | Nakagawa et al. | 260/288 R |
| 3,957,806 | 5/1976 | Yale et al. | 260/296 R |

FOREIGN PATENT DOCUMENTS

| | | | |
|---|---|---|---|
| 39-19649 | 9/1964 | Japan. | |
| 1058822 | 1967 | United Kingdom | 260/288 |

OTHER PUBLICATIONS

Roth, H. and R. Rohrbach, Archiv. Pharm 303, p. 571 (1970).
Banjeree, D. et al., Indian J. Chem., vol. 8, Aug. 1970, p. 708.

Primary Examiner—Donald G. Daus
Assistant Examiner—Lisa Jones
Attorney, Agent, or Firm—John J. Kolano; Thomas R. Boland

[57] ABSTRACT

Cardiac arrhythmias can be treated by administering an effective amount of 3-aryloxy-1-(2-or 4-iminodihydro-1-pyridyl)-2-propanol or phamaceutically acceptable acid addition compound. Many new effective compounds of this type are disclosed.

9 Claims, No Drawings

3-ARYLOXY-1-(2- OR 4-IMINODIHYDRO-1-PYRIDYL)-2-PROPANOL ANTIARRHYTHMIC COMPOUNDS

BACKGROUND OF THE INVENTION

This invention relates to improved methods for treatment of cardiac arrhythmias, and more particularly, to novel compounds useful in the treatment of cardiac arrhythmias.

Cardiac arrhythmia may be defined as a variation from the normal rhythm of the heart beat. Different types of arrhythmias are recognized according to the portion of the heart which is affected and the way in which the beat departs from the norm. Thus, atrial flutter and fabrillation, ventriculator flutter and fibrillation, sinus tachycardia and sinus bradycardia are representative arrhythmias.

Cardiac arrhythmias are usually treated by administering drugs which help to restore the normal heartbeat. Such drugs as quinidine, procainamide, lidocaine, and propranolol have been used with some success in treating cardiac arrhythmias. The drugs hitherto used in the therapy of cardiac arrhythmias each have been found to have significant limitations which have made the treatment less than optimally effective and safe. For example, each of the prior art drugs has frequently been found to be useful against only one type of cardiac arrhythmia. Also prior art drugs have generally had a short duration of activity, and have been found to produce undesirable side effects such as gastro intestinal distress, hypotension, myocardial depression, respiratory depression, and central nervous system (CNS) stimulation or depression.

Certain compounds structurally related to the novel compounds of this invention have been disclosed in the prior art.

1-Phenoxy-3-(2-imino-1,2-dihydropyridyl)-2-propanol is disclosed by D. Banerjee, T. K. Das Gupta, S. Mukerji, and B. N. Mitra, *Indian J. Chem.*, 8, 707–709 (1970). The compound was synthesized as an intermediate in the preparation of 1-phenoxy-3-(2-amino-1-piperidine)-2-propanol, a potential anticancer agent. However, neither compound was found to have anticancer activity. No other utility is disclosed by these authors.

1-Phenoxy-3-(2-imino-3-methyl-1,2-dihydropyridyl)-2-propanol is disclosed in H. J. Roth and R. Rohrbach, *Archiv. Pharm.*, 303, 563–578 (1970). The compound was synthesized in the course of a series of experiments on reactions of substituted pyridines with 1,2-epoxides. No utility is disclosed for the compound.

3-(2-methylphenoxy)-1-(2-imino-1,2-dihydropyridyl)-2-propanol is disclosed in Y. M. Beasley, V. Petrow, and O. Stephenson, *J. Pharm. and Pharmacol.*, 10, 47–59 (1958); K. Okamoto and M. Tetsuo, *Yakugaku Zasshi*, 82, 769–770 (1962); and Japanese Pat. No. 19, 649 (64), issued Sept. 11, 1964. Beasley, et al., mistakenly identify the compound as 3-(2-methylphenoxy)-1-(2-pyridylamino)-2-propanol. They prepared the compound int the course of a search for new analgesics, but no analgesic properties are attributed to this compound. Okamoto, et al., and the Japanese patent both disclose the correct structure for this compound but neither discloses any utility for it.

Thus the prior art has disclosed these three compounds but has not disclosed any pharmacological utility for them.

SUMMARY OF THE INVENTION

It is an object of this invention to provide an improved pharmaceutical treatment for cardiac arrhythmias by utilizing a 3-aryloxy-1-(2- or 4-iminodihydro-1-pyridyl)-2-propanol.

A further object of this invention is to provide novel chemical compounds suitable for use as antiarrhythmic drugs. A further object is to provide compounds having "broad-spectrum" antiarrhythmic activity, that is activity against more than one kind of arrhythmia. A further object is to provide compounds having a long duration of antiarrhythmic activity.

It has now been discovered that the objects of the invention can be attained by administering a therapeutically effective dose of a 3-aryloxy-1-(2- or 4-iminodihydro-1-pyridyl)-2-propanol having the structural formula:

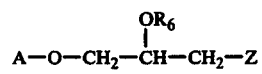

wherein:

A is an aromatic radical selected from the group consisting of:
(a) substituted phenyl groups having the formula:

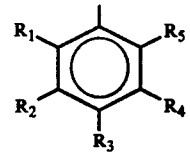

wherein $R_1$, $R_2$, $R_3$, $R_4$, and $R_5$, which may be the same or different, are substituents selected from the group consisting of:
hydrogen,
alkyl,
alkenyl,
alkynyl,
cycloalkyl,
phenyl,
alkoxy,
halo,
hydroxy,
hydroxymethyl,
amino,
acyloxy,
acylamino,
acylalkylamino,
dialkylamino,
trifluoromethyl,
nitro,
cyano,
acyl,
formyl,
carboxy,
alkoxycarbonyl,
carbamoyl,
alkylaminosulfonyl,
alkylsulfonyl,
alkoxyalkyl,
carboxyalkyl,
carbamoylalkyl,
alkoxyalkoxy, provided that at least one of $R_1$, $R_2$, $R_3$, $R_4$, and $R_5$ must be hydrogen, no more than 4 may be loweralkyl, no more than three may be loweralkoxy, no more than 2 may be halogen, and no more than 1 may be any of the other substituents; and the total carbon content of all the substituents must not exceed 6 carbon atoms;

(b) naphthyl and naphthyl substituted with no more than two alkyl groups and no more than one other substituent selected from the group consisting of
halo,
alkoxy,
nitro,
aminosulfonyl,
acylamino,
provided that the total carbon content of all the substituents must not exceed 4 carbon atoms;

(c) polycyclic carbocyclic radicals selected from the group consisting of
indenyl,
indanyl,
5,6,7,8-tetrahydronaphthyl,
6,7,8,9-tetrahydro-5H-benzocycloheptenyl,
5,6,7,8,9,10-hexahydrobenzocyclooctenyl,
5,6,7,8-tetrahydro-5,8-methano-1-naphthyl,
5,6,7,8-tetrahydro-5,8-ethano-1-naphthyl,
1,2,3,4-tetrahydro-1-oxo-5-naphthyl; and (d) bicyclic heterocyclic radicals selected from the group consisting of
4-benzofuranyl,
7-benzofuranyl,
2-acetyl-7-benzofuranyl,
4-benzothienyl,
7-benzothienyl,
8-coumarinyl,
5-methyl-8-coumarinyl,
8-thiochromanyl,
5-quinolyl,
5-isoquinolyl;

Z is an iminodihydropyridyl radical having the structural formula

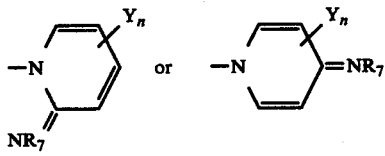

wherein:
Y is selected from the group consisting of
hydrogen,
loweralkyl,
loweralkenyl,
loweralkoxy,
alkoxycarbonyl,
loweracyl,
loweracyloxy,
loweracylamino,
carbamoyl,
cyano,
halo,
nitro,
hydroxymethyl,
hydroxy,
carboxy,
amino,
and n = 1 or 2 when Y is loweralkyl or halo and n = 1 in all other cases;

$R_6$ is selected from the group consisting of
hydrogen,
loweralkoxycarbonyl,
loweracyl,
carboxyloweracyl,
carbamoyl,
thiocarbamoyl; and
$R_7$ is selected from the group consisting of
hydrogen,
loweralkyl,
loweralkenyl,
loweralkynyl,
$C_3$–$C_6$ cycloalkyl,
$C_4$–$C_8$ cycloalkylalkyl,
phenyl,
benzyl,
phenylethyl,
loweralkoxycarbonyl,
loweracyl,
carboxyloweracyl,
carbamoyl,
thiocarbamoyl;
and pharmaceutically acceptable acid addition compounds.

"Lower" in the above definition is to be taken as encompassing up to 6 carbon atoms.

Treatment of cardiac arrhythmias with these compounds is an improvement over the prior art. Many of the compounds of this invention are effective against both atrial and ventricular arrhythmias and have a prolonged antiarrhythmic action.

The novel compounds of this invention have the structural formula:

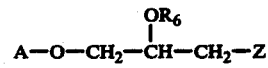

wherein:
A is an aromatic radical selected from the group consisting of: (a) substituted phenyl groups having the formula:

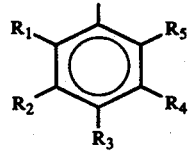

where $R_1$, $R_2$, $R_3$, $R_4$, and $R_5$, which may be the same or different, are substituents selected from the group consisting of:
hydrogen,
alkyl,
alkenyl,
alkynyl,
cycloalkyl,
phenyl,
alkoxy,
halo,
hydroxy,
hydroxymethyl,
amino,
acyloxy,
acylamino, acylalkylamino,
dialkylamino,
trifluoromethyl,
nitro,
cyano,
acyl,
formyl,
carboxy,
alkoxycarbonyl,
carbamoyl,
alkylaminosulfonyl,
alkylsulfonyl,
alkoxyalkyl,
carboxyalkyl,
carbamoylalkyl,
alkoxyalkoxy,
provided that at least one of $R_1$, $R_2$, $R_3$, $R_4$ and $R_5$ must be hydrogen, no more than 4 may be loweralkyl, no more than three may be loweralkoxy, no more than 2 may be halogen, and no more than one may be any of the other substituents; and the total carbon content of all the substituents must not exceed 6 carbon atoms and provided that A is not phenyl or o-tolyl when Z is

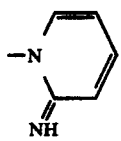

and A is not phenyl when Z is

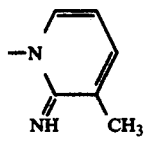

(b) naphthyl and naphthyl substituted with no more than two alkyl groups and no more than one other substituent selected from the group consisting of
halo,
alkoxy,
nitro,
aminosulfonyl,
acylamino,
provided that the total carbon content of all the substituents must not exceed 4 carbon atoms;
(c) polycyclic carbocyclic radicals selected from the group consisting of
indenyl,
indanyl,
5,6,7,8-tetrahydronaphythyl,
6,7,8,9-tetrahydro-5H-benzocycloheptenyl,
5,6,7,8,9,10-hexahydrobenzocyclooctenyl,
5,6,7,8-tetrahydro-5,8-methano-1-naphthyl,
5,6,7,8-tetrahydro-5,8-ethano-1-naphthyl,
1,2,3,4-tetrahydro-1-oxo-5-naphthyl; and
(d) bicyclic heterocyclic radicals selected from the group consisting of
4-benzofuranyl,
7-benzofuranyl,
2-acetyl-7-benzofuranyl,
4-benzothienyl,
7-benzothienyl,
8-coumarinyl,
5-methyl-8-coumarinyl,
8-thiochromanyl,
5-quinolyl,
5-isoquinolyl;
Z is an iminodihydropyridyl radical having the structural formula

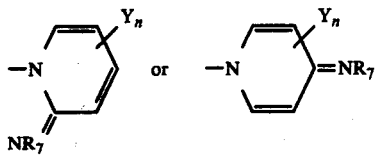

wherein:
Y is selected from the group consisting of
hydrogen,
loweralkyl,
loweralkenyl,
loweralkoxy,
carboalkoxy,
loweracyl,
loweracyloxy,
loweracylamino,
carbamoyl,
cyano,
halo,
nitro,
hydroxymethyl,
hydroxy,
carboxy,
amino,
and n = 1 or 2 when Y is loweralkyl or halo and n = 1 in all other cases;
$R_6$ is selected from the group consisting of
hydrogen,
loweralkoxycarbonyl,
loweracyl,
carboxyloweracyl,
carbamoyl,
thiocarbamoyl,
$R_7$ is selected from the group consisting of
hydrogen,
loweralkyl,
loweralkenyl,
loweralkynyl,
$C_3$-$C_6$ cycloalkyl,
$C_4$-$C_8$ cycloalkylalkyl,
phenyl,
benzyl,
phenylethyl,
loweralkoxycarbonyl,
loweracyl,
carboxyloweracyl,
carbamoyl,
thiocarbamoyl,
and pharmaceutically acceptable acid addition compounds. The term "acid addition compound" refers to ordinary acid addition salts of the type, for example,

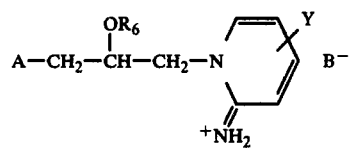

wherein B⁻ signifies the anion of the acid, and to compounds of the type in which the elements of the acid add across the double bond between carbon and nitrogen to form a compound of the type

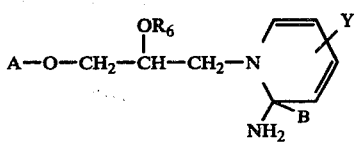

"Lower" in the above definition is to be taken as encompassing up to 6 carbon atoms.

DESCRIPTION OF THE PREFERRED EMBODIMENTS

Representative radicals which may be incorporated as group A in the novel compounds of this invention include phenyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-n-butylphenyl, 3-n-butylphenyl, 4-n-butylphenyl, 2-(1-methylpropyl)phenyl, 3-(1-methylpropyl)phenyl, 4-(1-methylpropyl)phenyl, 2-isobutylphenyl, 3-isobutylphenyl, 4-isobutylphenyl, 2-t-butylphenyl, 3-t-butylphenyl, 4-t-butylphenyl, 2-n-pentylphenyl, 3-n-pentylphenyl, 4-n-pentylphenyl, 2-(1-methylbutyl)phenyl, 3-(1-methylbutyl)phenyl, 4-(1-methylbutyl)phenyl, 2-(2-methylbutyl)phenyl, 3-(2-methylbutyl)phenyl, 4-(2-methylbutyl)phenyl, 2-(3-methylbutyl)phenyl, 3-(3-methylbutyl)phenyl, 4-(3-methylbutyl)phenyl, 2-(2,2-dimethylpropyl)phenyl, 3-(2,2-dimethylpropyl)phenyl, 4-(2,2-dimethylpropyl)phenyl, 2-n-hexylphenyl, 3-n-hexylphenyl, 4-n-hexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethyl, 2,4,5-trimethylphenyl, 2,4,6-trimethylphenyl, 2,3,4,5-tetramethylphenyl, 2,3,4,6-tetramethylphenyl, 2,3,5,6-tetramethylphenyl, 2,3,4,5,6-pentamethylphenyl, 2-ethyl-3-methylphenyl, 2-ethyl-4-methylphenyl, 2-ethyl-5-methylphenyl, 2-ethyl-6-methylphenyl, 2,3-diethylphenyl, 2,4-diethylphenyl, 2-propyl-3-ethylphenyl, 2-vinylphenyl, 3-vinylphenyl, 4-vinylphenyl, 2-allylphenyl, 3-allylphenyl, 4-allylphenyl, 2-ethynylphenyl, 3-ethynylphenyl, 4-ethynylphenyl, 3-cyclopropylphenyl, 4-cyclopropylphenyl, 2-biphenylyl, 3-biphenylyl, 4-biphenylyl, 2-methoxyphenyl, 3-methoxyphenyl, 4-methoxyphenyl, 2-ethoxyphenyl, 3-ethoxyphenyl, 4-ethoxyphenyl, 2-n-propoxyphenyl, 3-n-propoxyphenyl, 4-n-propoxyphenyl, 2-isopropoxyphenyl, 3-isopropoxyphenyl, 4-isopropoxyphenyl, 4-n-butoxyphenyl, 4-t-butoxyphenyl, 2-allyloxyphenyl, 3-allyloxyphenyl, 4-allyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,4,5-trimethoxyphenyl, 2,3,6-trimethoxyphenyl, 2,4,6-trimethoxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, 2-hydroxyphenyl, 3-hydroxyphenyl, 4-hydroxyphenyl, 2-hydroxymethylphenyl, 3-hydroxymethylphenyl, 4-hydroxymethylphenyl, 2-aminophenyl, 3-aminophenyl, 4-aminophenyl, 2-nitrophenyl, 3-nitrophenyl, 4-nitrophenyl, 2-cyanophenyl, 3-cyanophenyl, 4-cyanophenyl, 2-formylphenyl, 3-formylphenyl, 4-formylphenyl, 2-acetylphenyl, 3-acetylphenyl, 4-acetylphenyl, 2-acetoxyphenyl, 3-acetoxyphenyl, 4-acetoxyphenyl, 2-carboxyphenyl, 3-carboxyphenyl, 4-carboxyphenyl, 2-(methoxycarbonyl)phenyl, 3-(methoxycarbonyl)phenyl, 4-(methoxycarbonyl)phenyl, 2-carbamoylphenyl, 3-carbamoylphenyl, 4-carbamoylphenyl, 2-dimethylaminophenyl, 2-acetylaminophenyl, 2-(acetyl)methylaminophenyl, 2-methylsulfonylphenyl, 3-methylsulfonylphenyl, 4-methylsulfonylphenyl, 2-methylsulfonamidophenyl, 3-methylsulfonamidophenyl, 4-methylsulfonamidophenyl, 2-(2-methoxyethyl)phenyl, 3-(2-methoxyethyl)phenyl, 4-(2-methoxyethyl)phenyl, 2-(2-carboxyethyl)phenyl, 3-(carboxyethyl)phenyl, 4-(carboxyethyl)phenyl, 2-(carbamoylmethyl)phenyl, 3-(carbamoylmethyl)phenyl, 4-(carbamoylmethyl)phenyl, 2-(2-methoxyethoxy)phenyl, 3-(2-methoxyethoxy)phenyl, 4-(2-methoxyethoxy)phenyl, 2-methyl-3-methoxyphenyl, 2-methyl-4-methoxyphenyl, 2-methyl-5-methoxyphenyl, 2-methyl-6-methoxyphenyl, 2-methoxy-3-methylphenyl, 2-methoxy-4-methylphenyl, 2-methoxy-5-methylphenyl, 1-naphthyl, 2-naphthyl, 2-methyl-1-naphthyl, 3-methyl-1-naphthyl, 4-methyl-1-naphthyl, 5-methyl-1-naphthyl, 6-methyl-1-naphthyl, 7-methyl-1-naphthyl, 8-methyl-1-naphthyl, 2-ethyl-1-naphthyl, 4-ethyl-1-naphthyl, 4-butyl-1-naphthyl, 2,3-dimethyl-1-naphthyl, 2,4-dimethyl-1-naphthyl, 2,5-dimethyl-1-naphthyl, 1-methyl-2-naphthyl, 3-methyl-2-naphthyl, 6-methyl-2-naphthyl, 2-chloro-1-naphthyl, 3-chloro-1-naphthyl, 4-chloro-1-naphthyl, 5-chloro-1-naphthyl, 6-chloro-1-naphthyl, 7-chloro-1-naphthyl, 8-chloro-1-naphthyl, 2-fluoro-1-naphthyl, 4-fluoro-1-naphthyl, 2-bromo-1-naphthyl, 4-bromo-1-naphthyl, 1-chloro-2-naphthyl, 4-chloro-2-naphthyl, 2-methoxy-1-naphthyl, 3-methoxy-1-naphthyl, 4-methoxy-1-naphthyl, 5-methoxy-1-naphthyl, 6-methoxy-1-naphthyl, 7-methoxy-1-naphthyl, 8-methoxy-1-naphthyl, 4-ethoxy-1-naphthyl, 4-n-butoxy-1-naphthyl, 1-methoxy-2-naphthyl, 4-methoxy-2-naphthyl, 6-methoxy-2-naphthyl, 3-nitro-1-naphthyl, 4-nitro-1-naphthyl, 4-aminosulfonyl-1-naphthyl, 4-acetylamino-1-naphthyl, indenyl, indanyl, 5,6,7,8-tetrahydronaphthyl, 6,7,8,9-tetrahydro-5H-benzocycloheptenyl, 5,6,7,8,9,10-hexahydrobenzocyclooctenyl, 5,6,7,8-tetrahydro-5,8-methano-1-naphthyl, 5,6,7,8-tetrahydro-5,8-ethano-1-naphthyl, 1,2,3,4-tetrahydro-1-oxo-5-naphthyl, 4-benzofuranyl, 7-benzofuranyl, 2-acetyl-7-benzofuranyl, 4-benzothienyl, 7-benzothienyl, 8-coumarinyl, 5-methyl-8-coumarinyl, 8-thiochromanyl, 5-quinolyl, and 5-isoquinolyl.

Preferred groups for A in the antiarrhythmic compounds of this invention include substituted phenyl groups such as 2-ethylphenyl, 2,3-dimethylphenyl, 2-allylphenyl, 4-ethynylphenyl, 4-cyclohexylphenyl, 2-cyclohexylphenyl, 2-ethoxyphenyl, 3-ethoxyphenyl, 4-ethoxyphenyl, 2-chlorophenyl, 3-chlorophenyl, 4-chlorophenyl, 2-fluorophenyl, 3-fluorophenyl, 4-fluorophenyl, 3-acetoxyphenyl, 4-acetylaminophenyl, 4-dimethylaminophenyl, 2-trifluoromethylphenyl, 3-acetylphenyl, 3-methoxycarbonylphenyl, 4-carbamoylphenyl, 4-methylaminosulfonylphenyl, 4-(2-methoxyethyl)phenyl, 4-carboxymethylphenyl, 4-carbamoylmethylphenyl, 4-(2-methoxyethoxy)phenyl, 1-naphthyl, 4-indanyl, and 5-indanyl. More preferred groups are 4-allylphenyl, 4-acetylaminophenyl, 4-carbamoylphenyl, 4-(2-methoxyethyl)phenyl, 4-(2-methoxyethoxy)phenyl, 1-naphthyl, 4-indanyl, and 5-indanyl. Suitable groups for Z in the compounds of this invention include 2-imino-1,2-dihydro-1-pyridyl, 4-imino-1,4-dihydro-1-pyridyl, 2-imino-1,2-dihydro-3-methyl-1-pyridyl, 2-imino-1,2-dihydro-4-methyl-1-pyridyl, 2-imino-1,2-dihydro-5-methyl-1-pyridyl, 2-imino-1,2-dihydro-6-methyl-1-pyridyl, 2-imino-1,2-dihydro-3-ethyl-1-pyridyl, 2-imino-1,2-dihydro-4-propyl-1-pyridyl, 2-imino-1,2-dihydro-4-t-butyl-1-pyridyl, 2-imino-1,2-dihydro-4-allyl-1-pyridyl, 2-imino-1,2-dihydro-3-methoxy-1-pyridyl, 2-imino-1,2-dihydro-4-methoxy-1-pyridyl, 2-dihydro-5-methoxy-1-pyridyl, 2-imino-1,2-dihydro-6-methoxy-1-pyridyl, 2-imino-1,2-dihydro-3-ethoxy-1-pyridyl, 2-imino-1,2-dihydro-3-methoxycarbonyl-1-pyridyl, 2-imino-1,2-dihydro-4-methoxycarbonyl 1-pyridyl, 2-imino-1,2-dihydro-4-ethoxycarbonyl-1-pyridyl, 2-imino-1,2-dihydro-3-carbamoyl-1-pyridyl, 2-imino-1,2-dihydro-4-acetyl-1-pyridyl, 2-imino-1,2-dihydro-4-acetoxy-1-pyridyl, 2-imino-1,2-dihydro-4-acetylamino-1-pyridyl, 2-imino-1,2-dihydro-4-carbamoyl-1-pyridyl, 2-imino-1,2-dihydro-4-cyanopyridyl, 2-imino-1,2-dihydro-3-chloro-1-pyridyl, 2-imino-1,2-dihydro-4-chloro-1-pyridyl, 2-imino-1,2-dihydro-5-chloro-1-pyridyl, 2-imino-1,2-dihydro-6-chloro-1-pyridyl, 2-imino-1,2-dihydro-3-fluoro-1-pyridyl, 2-imino-1,2-dihydro-4-fluoro-1-pyridyl, 2-imino-1,2-dihydro-4-bromo-1-pyridyl, 2-imino-1,2-dihydro-3,5-dichloro-1-pyridyl, 2-imino-1,2-dihydro-4-nitro-1-pyridyl, 2-imino-1,2- dihydro-4-hydroxymethyl-1-pyridyl, 2-imino-1,2-dihydro-4-carboxy-1-pyridyl, 2-imino-1,2-dihydro-4-amino-1-pyridyl, 2-methylimino-1,2-dihydro-1-pyridyl, 2-ethylimino-1,2-dihydro-1-pyridyl, 2-n-propylimino-1,2-dihydro-1-pyridyl, 2-isopropylimino-1,2-dihydro-1-pyridyl, 2-n-butylimino-1,2-dihydro-1-pyridyl, 2-isobutylimino-1,2-dihydro-1-pyridyl, 2-t-butylimino-1,2-dihydro-1-pyridyl, 2-n-pentylimino-1,2-dihydro-1-pyridyl, 2-n-hexylimino-1,2-dihydro-1-pyridyl, 2-allylimino-1,2-dihydro-1-pyridyl, 2-(2-buten-1-yl)-1,2-dihydro-1-pyridyl, 2-propargylimino-1,2-dihydro-1-pyridyl, 2-cyclopropylimino-1,2-dihydro-1-pyridyl, 2-cyclobutylimino-1,2-dihydro-1-pyridyl, 2-cyclopentylimino-1,2-dihydro-1-pyridyl, 2-cyclohexylimino-1,2-dihydro-1-pyridyl, 2-cyclopropylmethylimino-1,2-dihydro-1-pyridyl, 2-cyclohexylmethyl-1,2-dihydro-1-pyridyl, 2-(2-cyclohexylethyl)imino-1,2-dihydro-1-pyridyl, 2-phenylimino-1,2-dihydro-1-pyridyl, 2-benzylimino-1,2-dihydro-1-pyridyl, 2-(1-phenylethyl)imino-1,2-dihydro-1-pyridyl, 2-(2-phenylethyl)imino-1,2-dihydro-1-pyridyl, 2-methoxycarbonylimino-1,2-dihydro-1-pyridyl, 2-ethoxycarbonyl, imino-1,2-dihydro-1-pyridyl, 2-acetylimino-1,2-dihydro-1-pyridyl, 2-propionylimino-1,2-dihydro-1-pyridyl, 2-n-butyrylimino-1,2-dihydro-1-pyridyl, 2-isobutyrylimino-1,2-dihydro-1-pyridyl, 2-(3-carboxypropionyl)imino-1,2-dihydro-1-pyridyl, 2-carbamoylimino-1,2-dihydro-1-pyridyl, and 2-thiocarbamoylimino-1,2-dihydro-1-pyridyl.

Suitable groups for $R_6$ in the compounds of this invention are hydrogen, methoxycarbonyl, ethoxycarbonyl, propoxycarbonyl, butoxycarbonyl, acetyl, propionyl, butyryl, benzoyl, 3-carboxypropionyl, 3-carboxyacrylyl, 2-carboxybenzoyl, 3-methoxycarbonylpropionyl, carbamoyl, N-methylcarbamoyl, thiocarbamoyl, 4-carboxy-3-oxobutyryl, 4-carboxy-2,2-dimethylbutyryl, 4-carboxy-3,3-dimethylbutyryl, 3-carboxy-2,3-dimethylacrylyl, 2-carboxymethyl-4-tetradecenoyl, heptafluorobutylryl, 4-carboxy-3-methylbutyryl, 3-carboxy-2-methylpropionyl, 4-carboxy-4-phenylbutyryl, 9-carboxy-3,8-di(carboxymethyl)nonanoyl, (2-carboxyphenyl)acetyl, 3-carboxy-1-2,2-trimethylcyclopentylcarbonyl, 2-carboxy-1-cyclobutylcarbonyl, 2-carboxycyclohexylcarbonyl, 3-carboxy-2-nicotinoyl.

Preferred groups for $R_6$ are hydrogen, methoxycarbonyl, 3-carboxypropionyl, 3-carboxyacrylyl, and 2-carboxybenzoyl.

Preferred groups for Z include 2-imino-1,2-dihydropyridyl groups having the formula

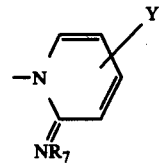

wherein Y is selected from the group consisting of hydrogen, loweralkyl, and loweralkoxy, and $R_7$ is selected from the group consisting of hydrogen, loweralkyl, and loweralkoxycarbonyl.

By combination of the groups defined above for A and Z different antiarrhythmic compounds can be prepared. The preferred compounds are those in which A is selected from the group consisting of 2-ethylphenyl, 2,3-dimethylphenyl, 4-allylphenyl, 4-ethynylphenyl, 4-cyclohexylphenyl, 2-cyclohexylphenyl, 2-ethoxyphenyl, 3-ethoxyphenyl, 4-ethoxyphenyl, 2-chlorophenyl, 3-chlorophenyl, 4-chlorophenyl, 2-fluorophenyl, 3-fluorophenyl, 4-fluorophenyl, 3-acetoxyphenyl, 4-acetylaminophenyl, 4-dimethylaminophenyl, 2-trifluoromethylphenyl, 3-acetylphenyl, 3-methoxycarbonylphenyl, 4-carbamoylphenyl, 4-methylaminosulfonylphenyl, 4-(2-methoxyethyl)phenyl, 4-carboxymethylphenyl, 4-carbamoylmethylphenyl, 4-(2-methoxyethoxy)phenyl 1-naphthyl, 4-indanyl, and 5-indanyl: Z is selected from the group consisting of 2-imino-1,2-dihydropyridyl radicals having the formula

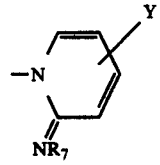

wherein Y is selected from the group consisting of hydrogen, loweralkyl, and loweralkoxy; $R_7$ is selected from the group consisting of hydrogen, loweralkyl, loweracyl and loweralkoxycarbonyl and $R_6$ is selected from the group consisting of hydrogen, methoxycarbonyl, and loweracyl.

The antiarrhythmic compounds of this invention may be synthesized by reacting an aryloxy-1,2-epoxypropane with a suitably substituted 2-aminopyridine in a 90:10 mixture of methanol and water at room temperature. The reaction may be represented by the equation:

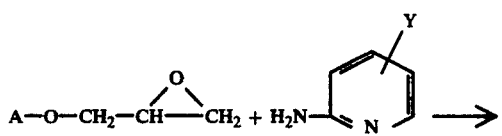

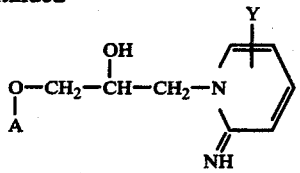

The reaction is complete in a few days, and the product is isolated by procedures well known to those skilled in the art.

The aryloxy-1,2-epoxypropane may be prepared by reacting a suitable phenol or naphthol with epichlorohydrin in aqueous alkaline solution according to procedures well known in the art. A description of the procedure for synthesis of the aryloxy-1,2-epoxypropanes may be found in Beasley, et al., *J. Pharm. Pharmacol.* 10, 47–59 (1958).

Compounds with various substituents on the aromatic nucleus of the A groups can be prepared from the corresponding phenols or naphthols by the procedure of Beasley, et al.

Likewise, Z groups having various Y substituents can be prepared by starting with the appropriately substituted 2-aminopyridine.

Compounds wherein $R_7$ is loweralkyl can be prepared by using an N-alkyl-2-aminopyridine as the starting material for the synthesis. Compounds wherein $R_7$ is loweralkyl can also be prepared by direct alkylation of the corresponding compound having $R_7=H$ by reaction with the customary alkylating agents such as alkyl halides, alkyl p-toluenesulfonates, and the like.

Compounds wherein $R_6$ or $R_7$ is alkoxycarbonyl, acyl, carboxyacyl, carbamoyl or thiocarbamoyl may be prepared by reacting the corresponding compound wherein $R_6$ or $R_7$ is hydrogen with a suitable reagent. To prepare the alkoxycarbonyl and acyl derivatives alkyl chloroformates, acyl halides, or anhydrides of lower carboxylic acids may be used. To prepare the carboxyacyl derivatives, cyclic anhydrides, such as succinic anhydride, maleic anhydride, and phthalic anhydride are suitable. To prepare carbamoyl, n-alkylcarbamoyl, thiocarbamoyl, and n-alkylthiocarbamoyl derivatives, the corresponding isocyanate or isothiocyanate may be used. If both $R_6$ and $R_7$ are to be converted to the derivative, two moles of reagent are reacted with one mole of the corresponding 2-propanol. If only one of $R_6$ and $R_7$ is to be converted, one mole of reagent is used. It will be understood that to prepare derivatives having only one of $R_6$ and $R_7$ derivatized the reaction conditions may have to be adjusted to favor reaction at either $R_6$ or $R_7$.

The compounds in which Z is a 4-imino-1,4-dihydro-1-pyridyl radical may be prepared in the same way as those in which Z is a 2-imino-1,2-dihydro-1-pyridyl group by using an appropriately substituted 4-aminopyridine as a reagent in place of the 2-aminopyridine in the reaction described above.

The compounds of this invention may be converted to their pharmaceutically acceptable acid addition salts by methods customary in the art. The pharmaceutically acceptable salts of this invention are those salts, the acid component of which is pharmacologically acceptable in the intended dosages. Suitable salts are those prepared from inorganic acids or organic acids. Such acids include: hydrochloric acid, hydrobromic acid, nitric acid, sulfuric acid, sulfamic acid, the polyphosphoric acids, phosphoric acid, glycerophosphoric acid, acetic acid, propionic acid, butyric acid, succinic acid, glycolic acid, 2,3-dihydroxypropionic acid, saccharic acid, gluconic acid, lactobionic acid, phenylacetic acid, cyclohexanecarboxylic acid, maleic acid, fumaric acid, lactic acid, citric acid, malic acid, camphoric acid, benzoic acid, tartaric acid, aspartic acid, salicyclic acid, phthalic acid, methanesulfonic acid, ethanesulfonic acid, benzenesulfonic acid, toluenesulfonic acid, nicotinic acid, ascorbic acid and the like. Preferred acids are hydrochloric, hydrobromic, acetic, benzoic and p-toluenesulfonic.

The compounds of this invention possess one or more asymmetric carbon atoms and consequently can be obtained as racemic mixtures or as dextro- (+) and levorotatory (−) isomers. These may be separated by any of the known methods of resolution. A method that may be employed is combining the racemic modification with an optically active acid, for example by salt formation. Two products are then obtained. If the compounds of this invention are added to an optically active acid such as (+) or (−) tartaric acid, then the salts produced possess different properties and different solubilities and can be separated by fractional crystallization. When the salts have been separated by repeated crystallization, the acid is split off and the pure (+) or (−) isomer is obtained. It is to be understood that these optical isomers are embraced within the extent of this invention. Likewise the configuration about the 2-imino group in the Z portion of the compounds of this invention may be syn or anti depending on the orientation of $R_7$ with respect to the nitrogen atom of the 2-amino-1,2-dihydro-1-pyridyl ring. Both configurations are included among the compounds of this invention.

The antiarrhythmic compounds of this invention were evaluated in vivo for their effect against different types of standard experimentally produced cardiac arrhythmias.

The effectiveness of the compounds against ouabain-induced ventricular tachycardia was evaluated by the following procedure.

Mongrel dogs of either sex weighing between 7 and 12 kg were anesthetized with sodium pentobarbital, 30 mg/kg, i.v. The femoral artery was cannulated and arterial blood pressure measured via a pressure transducer connected to a strip chart recorder. Mean arterial pressure was derived electronically. The right vagus nerve was sectioned and its distal end stimulated at a frequency of 50 cycles per second. The stimulation voltage was determined for each animal prior to drug administration and was in the range of 3 to 4 volts. Throughout the experiment, Lead II electrocardiogram was continuously recorded.

The antiarrhythmic activity of standard and unknown compounds was determined according to a modification of the method of Lucchesi and Hardman *J. Pharmacol Exp. Therap.* 13, 372–81, 1961. Ouabain was injected at a dose of 40 μg/kg followed in 30 minutes by injections of 10 μg/kg every 15 minutes until ventricular or nodal tachycardia occurred. The arrhythmia was shown to be independent of the sino-atrial pacemaker by the failure of right vagal stimulation to alter its rate. The ventricular rhythm was allowed to continue for 20 minutes and then the test drugs were administered. In control dogs, the untreated arrhythmia persisted for at least two hours.

Test drugs were administered by titration until the arrhythmia was reversed. The criteria for antiarrhythmic activity were:

(1) Reversion to normal sinus rhythm within a few minutes following drug administration (iv).

(2) Maintenance of sinus rhythm for 30 minutes or longer.

(3) Failure of right vagal stimulation to trigger ectopic ventricular beats.

In some of the animals, return of arrhythmia was produced by administering 40 units of intravenous insulin in order to demonstrate the continued presence of ouabain in sufficient concentrations to induce cardiac toxicity.

For intravenous administration drugs were dissolved in physiologic saline and given in a volume of 0.1 ml/kg. For oral administration drugs were delivered through a tube positioned in the stomach. For intraduodenal administration the abdomen was opened and a catheter positioned directly into the duodenum.

The effectiveness of the compounds against acetylcholine-induced ventricular fibrillation was determined by the following procedure.

Mongrel dogs unselected as to age or sex and ranging from 10 to 15 kg in weight were anesthetized by an intravenous injection of pentobarbital sodium, 30 mg/kg. In each dog a polyethylene cannula was inserted into the left femoral artery and connected to a transducer for blood pressure measurements. The left femoral vein was also catheterized for the purpose of drug injections. Artificial ventilation with room air was maintained by a Harvard positive-pressure respirator through a cuffed endotracheal tube.

Lead II electrocardiograms were monitored continuously on an oscilloscope and all recordings were made on an eight channel strip chart recorder.

After a mid-sternal thoracotomy, the pericardium was reflected from the right atrium and sutured to the thoracic wall to form a cradle. Selective atrial fibrillation was induced by applying a few drops of a 4% aqueous solution of acetylcholine directly to the right atrium through a 20 gauge needle and then stroking the atrial area a few times with a blunt spatula. The duration of atrial fibrillation was determined by noting on the electrocardiogram the time required for sinus rhythm to reappear.

After two control periods of fibrillation were obtained, drugs were then administered either intravenously, orally, or intraduodenally. Attempts were then made to reinduce atrial fibrillation at the following time intervals: 15, 30, 60 and 120 minutes after drug administration. A given dose of a drug was considered to be active if it significantly reduced the duration of the atrial arrhythmia at any of the above time intervals.

All drugs were administered as the free base and the results were analysed by Student's "T" test.

The effect of the compounds against ventricular arrhythmias after coronary ligation simulating myocardial infarction was determined by the following procedure.

Experimental myocardial infarction was produced in mongrel dogs (10–15kg) under general anaesthesia with sodium pentobarbital, 30 mg/kg, i.v., and under artifical respiration maintained with a Harvard positive-pressure respirator. Under aseptic conditions, the thorax was opened at the fourth intercostal space. The pericardium was incised and the anterior descending branch of the left coronary artery was dissected free about 8 mm distal to the edge of the left atrial appendage. Two silk ligatures were passed under the artery and the vessel was ligated in two stages according to the method described by A. S. Harris, Circulation 1, 1318 (1950). After closure of the pericardium and the thorax and when the respiration became spontaneous, the animal was maintained under supervision until awakening, 3 to 4 hours later.

The following day, eighteen hours post-surgery, the animals presented with a permanent extrasystolic arrhythmia. This arrhythmia was quantitated by counting every heart beat during a 5-minute period and noting the number of normal and abnormal depolarizations. All animals were studied in the unanesthetized state. Lead III electrocardiogram was continuously recorded while the animals were supported in a harness and maintained in a quiet environment. These animals were trained prior to surgery to lie quietly while ECG recordings were made. Drugs to be studied were injected directly into the brachial vein or were given orally contained in gelatin capsules. The criteria for inclusion into the study were as follows:

(1) The number of ectopic beats should be greater than 30% of the total number of beats per minute.

(2) The frequency of abnormal beats should remain constant for a two-hour monitoring period prior to drug administration.

After drug administration, the ECG was taken at 15-minute intervals for at least 4 hours. Results were recorded as percent reduction in the number of ectopic beats.

All of the compounds of this invention showed some antiarrhythmic activity in at least one of the above procedures.

The following examples are intended to illustrate the practice of this invention without limiting its scope.

EXAMPLE I

This example illustrates the synthesis of 3-(1-naphthoxy)-1-(2-imino-1,2-dihydro-1-pyridyl)-2-propanol.

82.85 Grams (0.35 mole) of 3-chloro-1-(1-naphthoxy)-2-propanol and 32.94 grams (0.35 mole) of 2-aminopyridine were combined in 750 ml of isopropyl alcohol. 241.87 Grams (1.75 moles) of potassium carbonate were added to the mixture, and the mixture was heated to reflux temperature and maintained at this temperature for two days.

The reaction mixture was then filtered while hot and the isopropyl alcohol was removed by evaporation in vacuo. The residue was triturated with diethyl ether and collected on a filter (M.P. 144.5°–145.5° C.).

A small quantity of this compound was dissolved in methanol. The solution was acidified to pH 3 with aqueous HCl and evaporated to dryness in vacuo. The white crystalline residue was recrystallized from methanol to give 3-(1-naphthoxy)-1-(2-imino-1,2-dihydro-1-pyridyl)-2-propanol hydrochloride. M.P. 209°–212° C.

Another portion of the free base prepared above was suspended and dissolved in hot acetone, and an equivalent amount of glacial acetic acid was added. The salt precipitated as an oil which crystallized upon seeding. The precipitate was filtered and washed with acetone and ether to give 3-(1-naphthoxy)-1-(2-imino-1,2-dihydro-1-pyridyl)-2-propanol, acetic acid salt. M.P. 138°–141° C.

EXAMPLE II

This example illustrates another method of synthesizing 3-(1-naphthoxy)-1-(2-imino-1,2-dihydro-1-pyridyl)-2-propanol.

4.41 Grams (0.022 mole) of 3-(1-naphthoxy)-1,2-epoxypropane and 1.88 grams (0.020 mole) of 2-aminopyridine were combined in a solvent mixture of 2 ml of methanol and 0.2 ml of water and allowed to stand at room temperature for four days. A solid precipitate formed which was collected on a filter, washed with methanol/water and with water and dried. The compound was recrystallized from isopropyl alcohol. M.P. 144.5°–145.5° C. (uncorr.).

EXAMPLE III

This example illustrates the synthesis of a number of compounds of this invention.

By a procedure similar to that of Example I, using the reagents listed in columns 1 and 2 of Table I, the compounds listed in column 3 of Table I were prepared.

TABLE I

| COMPOUND # | REAGENTS | | PRODUCT |
|---|---|---|---|
| 4324 | 3-(1-naphthoxy)-1,2-epoxypropane | 2-amino-3-methylpyridine | 3-(1-naphthoxy)-1-(2-imino-1,2-dihydro-1-pyridyl)-2-propanol |
| 4322 | 3-(1-naphthoxy)-1,2-epoxypropane | 2-amino-4-methylpyridine | 3-(1-naphthoxy)-1-(2-imino-1,2-dihydro-4-methyl-1-pyridyl)-2-propanol |
| 4329 | 3-(1-naphthoxy)-1,2-epoxypropane | 2-amino-5-methylpyridine | 3-(1-naphthoxy)-1-(2-imino-1,2-dihydro-5-methyl-1-pyridyl)-2-propanol |
| 4320 | 3-(1-naphthoxy)-1,2-epoxypropane | 4-aminopyridine | 3-(1-naphthoxy)-1-(4-imino-1,4-dihydro-1-pyridyl)-2-propanol |
| 4327 | 3-(1-naphthoxy-1,2-epoxypropane | 2-methylaminopyridine | 3-(1-naphthoxy)-1-(2-methyl-imino-1,2-dihydro-1-pyridyl)-2-propanol |
| 4358 | 3-(2-naphthoxy)-1,2-epoxypropane | 2-aminopyridine | 3-(2-naphthoxy)-1-(2-imino-1,2-dihydro-1-pyridyl)-2-propanol |
| 4365 | 3-phenoxy-1,2-epoxypropane | 2-aminopyridine | 3-phenoxy-1-(2-imino-1,2-dihydro-1-pyridyl)-2-propanol |
| 4346 | 3-phenoxy-1,2-epoxypropane | 2-amino-3-methylpyridine | 3-phenoxy-1-(2-imino-1,2-dihydro-3-methyl-1-pyridyl)-2-propanol |
| 4310 | 3-(2-methylphenoxy)-1,2-epoxypropane | 2-aminopyridine | 3-(2-methylphenoxy)-1-(2-imino-1,2-dihydro-1-pyridyl)-2-propanol |
| 4349 | 3-(2-methylphenoxy)-1,2-epoxypropane | 2-amino-3-methylpyridine | 3-(2-methylphenoxy)-1-(2-imino-3-methyl-1,2-dihydro-1-pyridyl)-2-propanol |
| 4347 | 3-(3-methylphenoxy)-1,2-epoxypropane | 2-aminopyridine | 3-(3-methylphenoxy)-1-(2-imino-1,2-dihydro-1-pyridyl)-2-propanol |
| 4350 | 3-(2,3-dimethylphenoxy)-1,2-epoxypropane | 2-aminopyridine | 3-(2,3-dimethylphenoxy)-1-(2-imino-1,2-dihydro-1-pyridyl)-2-propanol |
| 4370 | 3-(2,4-dimethylphenoxy)-1,2-epoxypropane | 2-aminopyridine | 3-(2,4-dimethylphenoxy)-1-(2-imino-1,2-dihydro-1-pyridyl)-2-propanol |
| 4363 | 3-(2,5-dimethylphenoxy)-1,2-epoxypropane | 2-aminopyridine | 3-(2,5-dimethylphenoxy)-1-(2-imino-1,2-dihydro-1-pyridyl)-2-propanol |
| 4359 | 3-(2,6-dimethylphenoxy)-1,2-epoxypropane | 2-aminopyridine | 3-(2,6-dimethylphenoxy)-1-(2-imino-1,2-dihydro-1-pyridyl)-2-propanol |
| 4360 | 3-(3,4-dimethylphenoxy)-1,2-epoxypropane | 2-aminopyridine | 3-(3,4-dimethylphenoxy)-1-(2-imino-1,2-dihydro-1-pyridyl)-2-propanol |
| 4364 | 3-(3,5-dimethylphenoxy)-1,2-epoxypropane | 2-aminopyridine | 3-(3,5-dimethylphenoxy)-1-(2-imino-1,2-dihydro-1-pyridyl)-2-propanol |
| 4366 | 3-(2-ethylphenoxy)-1,2-epoxypropane | 2-aminopyridine | 3-(2-ethylphenoxy)-1-(2-imino-1,2-dihydro-1-pyridyl)-2-propanol |
| 4396 | 3-(2,3,5-trimethylphenoxy)-1,2-epoxypropane | 2-aminopyridine | 3-(2,3,5-trimethylpenoxy)-1-(2-imino-1,2-dihydro-1-pyridyl)-2-propanol |
| 4415 | 3-(4-methylphenoxy)-1,2-epoxypropane | 2-aminopyridine | 3-(4-methylphenoxy)-1-(2-imino-1,2-dihydro-1-pyridyl)-2-propanol |
| 4410 | 3-(2-n-propylphenoxy)-1,2-epoxypropane | 2-aminopyridine | 3-(2-n-propylphenoxy)-1-(2-imino-1,2-dihydro-1-pyridyl)-2-propanol |
| 4357 | 3-(2-t-butylphenoxy)-1,2-epoxypropane | 2-aminopyridine | 3-(2-t-butylphenoxy)-1-(2-imino-1,2-dihydro-1-pyridyl)-2-propanol |
| 4348 | 3-(4-methoxyphenoxy)-1,2-epoxypropane | 2-aminopyridine | 3-(4-methoxyphenoxy)-1-(2-imino-1,2-dihydro-1-pyridyl)-2-propanol |
| 4352 | 3-(2-chlorophenoxy)-1,2-epoxypropane | 2-aminopyridine | 3-(2-chlorophenoxy)-1-(2-imino-1,2-dihydro-1-pyridyl)-2-propanol |
| 4353 | 3-(4-chlorophenoxy)-1,2-epoxypropane | 2-aminopyridine | 3-(4-chlorophenoxy)-1-(2-imino-1,2-dihydro-1-pyridyl)-2-propanol |
| 4379 | 3-[1-(5,6,7,8-tetrahydronaphthoxy]-1,2-epoxypropane | 2-aminopyridine | 3-[1-(5,6,7,8-tetrahyddronaphthoxy)]-1-(2-imino-1,2-dihydro-1-pyridyl)-2-propanol |
| 4381 | 3-(4-indanyloxy)-1,2-epoxypropane | 2-aminopyridine | 3-(4-indanyloxy)-1-(2-imino-1,2-dihydro-1-pyridyl)-2-propanol |
| 4376 | 3-(4-chloronaphthoxy)-1,2-epoxypropane | 2-aminopyridine | 3-(4-chloronaphthoxy)-1-(2-imino-1,2-dihydro-1-pyridyl)-2-propanol |
| 4391 | 3-(1-naphthoxy)-1,2-epoxypropane | 2-amino-5-chloropyridine | 3-(1-naphthoxy)-1-(2-imino-1,2-dihydro-5-chloro-1-pyridyl)-2-propanol |
| 4403 | 3-(5-indanyloxy)-1,2-epoxypropane | 2-aminopyridine | 3-(5-indanyloxy)-1-(2-imino-1,2-dihydro-1-pyridyl)-2-propanol |
| 4392 | 3-(2-allyloxyphenoxy)-1,2-epoxypropane | 2-aminopyridine | 3-(4-allyloxyphenoxy)-1-(2-imino-1,2-dihydro-1-pyridyl)-2-propanol |
| 3472 | 3-(4-allylphenoxy)-1,2-epoxypropane | 2-aminopyridine | 3-(4-allylphenoxy)-1-(2-imino-1,2-dihydro-1-pyridyl)-2-propanol |
| 3420 | 3-(4-propargylphenoxy)-1,2-epoxy- | 2-aminopyridine | 3-(4-propargylphenoxy)-1-(2-imino-1,2- |

TABLE I-continued

| COMPOUND # | REAGENTS | | PRODUCT |
|---|---|---|---|
| 3427 | 3-(2-cyclopropylpenoxy)-1,2-epoxy-propane | 2-aminopyridine | 3-(2-cyclopropylphenoxy)-1-(2-imino-1,2-dihydro-1-pyridyl)-2-propanol |
| 3432 | 3-(4-cyclohexylpenoxy)-1,2-epoxy-propane | 2-aminopyridine | 3-(4-cyclohexylphenoxy)-1-(2-imino-1,2-dihydro-1-pyridyl)-2-propanol |
| 3460 | 3-(4-phenylphenoxy)-1,2-epoxy-propane | 2-aminopyridine | 3-(4-phenylphenoxy)-1-(2-imino-1,2-dihydro-1-pyridyl)-2-propanol |
| 3428 | 3-(4-fluorophenoxy)-1,2-epoxy-propane | 2-aminopyridine | 3-(4-fluorophenoxy)-1-(2-imino-1,2-dihydro-1-pyridyl)-2-propanol |
| 3442 | 3-(4-bromophenoxy)-1,2-epoxy-propane | 2-aminopyridine | 3-(4-bromophenoxy)-1-(2-imino-1,2-dihydro-1-pyridyl)-2-propanol |
| 3454 | 3-(4-hydroxymethylphenoxy)-1,2-epoxypropane | 2-aminopyridine | 3-(4-hydroxymethylphenoxy)-1-(2-imino-1,2-dihydro-1-pyridyl)-2-propanol |
| 3418 | 3-(4-acetoxyphenoxy)-1,2-epoxy-propane | 2-aminopyridine | 3-(4-acetoxyphenoxy)-1-(2-imino-1,2-dihydro-1-pyridyl)-2-propanol |
| 4404 | 3-(4-acetamidophenoxy)-1,2-epoxy-propane | 2-aminopyridine | 3-(4-acetamidophenoxy)-1-(2-imino-1,2-dihydro-1-pyridyl)-2-propanol |
| 3447 | 3-(4-dimethylaminophenoxy)-1,2-epoxypropane | 2-aminopyridine | 3-(4-dimethylaminophenoxy)-1-(2-imino-1,2-dihydro-1-pyridyl)-2-propanol |
| 3422 | 3-(3-trifluoromethylphenoxy)-1,2-epoxypropane | 2-aminopyridine | 3-(3-trifluoromethylphenoxy)-1-(2-imino-1,2-dihydro-1-pyridyl)-2-propanol |
| 3441 | 3-(4-nitrophenoxy)-1,2-epoxy-propane | 2-aminopyridine | 3-(4-nitrophenoxy)-1-(2-imino-1,2-dihydro-1-pyridyl)-2-propanol |
| 3456 | 3-(4-cyanophenoxy)-1,2-epoxy-propane | 2-aminopyridine | 3-(4-cyanophenoxy)-1-(2-imino-1,2-dihydro-1-pyridyl)-2-propanol |
| 3476 | 3-(4-acetylphenoxy)-1,2-epoxy-propane | 2-aminopyridine | 3-(4-acetylphenoxy)-1-(2-imino-1,2-dihydro-1-pyridyl)-2-propanol |
| 3421 | 3-(4-formylphenoxy)-1,2-epoxy-propane | 2-aminopyridine | 3-(4-formylphenoxy)-1-(2-imino-1,2-dihydro-1-pyridyl)-2-propanol |
| 3466 | 3-(4-methoxycarbonylphenoxy)-1,2-epoxypropane | 2-aminopyridine | 3-(4-methoxycarbonylphenoxy)-1-(2-imino-1,2-dihydro-1-pyridyl)-2-propanol |
| 3484 | 3-(4-carbamoylphenoxy)-1,2-epoxypropane | 2-aminopyridine | 3-(4-carbamoylphenoxy)-1-(2-imino-1,2-dihydro-1-pyridyl)-2-propanol |
| 3462 | 3-(4-methylsulfonylphenoxy)-1,2-epoxypropane | 2-aminopyridine | 3-(4-methylsulfonylphenoxy)-1-(2-imino-1,2-dihydro-1-pyridyl)-2-propanol |
| 3451 | 3-(4-methoxymethylphenoxy)-1,2-epoxypropane | 2-aminopyridine | 3-(4-methoxymethylphenoxy)-1-(2-imino-1,2-dihydro-1-pyridyl)-2-propanol |
| 3479 | 3-[4-(2-carbamoylethyl)phenoxy]-1,2-epoxypropane | 2-aminopyridine | 3-[4-(2-carbamoylethyl)phenoxy]-1-(2-imino-1,2-dihydro-1-pyridyl)-2-propanol |
| 3458 | 3-(4-nitro-1-naphthoxy)-1,2-epoxy-propane | 2-amiopyridine | 3-(4-nitro-1-naphthoxy)-1-(2-imino-1,2-dihydro-1-pyridyl)-2-propanol |
| 3437 | 3-(4-acetylamio-1-naphthoxy)-1,2-epoxypropane | 2-aminopyridine | 3-(4-acetylamino-1-naphthoxy)-1-(2-imino-1,2-dihydro-1-pyridyl)-2-propanol |
| 3480 | 3-(4-indenyloxy)-1,2-epoxypropane | 2-aminopyridine | 3-(4-indenyloxy)-1-(2-imino-1,2-dihydro-1-pyridyl)-2-propanol |
| 3473 | 3-(1,2,3,4-tetrahydro-1-oxo-5-naphthoxy)-1,2-epoxypropane | 2-aminopyridine | 3-(1,2,3,4-tetrahydro-1-oxo-5-naphthoxy)-1-(2-imino-1,2-dihydro-1-pyridyl)-2-propanol |
| 4414 | 3-(4-methoxy-1-naphthoxy)-1,2-epoxy-propane | 2-amiopyridine | 3-(4-methoxy-1-naphthoxy)-1-(2-imino-1,2-dihydro-1-pyridyl)-2-propanol |
| 3468 | 3-(7-benzofuranyloxy)-1,2-epoxy-propane | 2-aminopyridine | 3-(7-benzofuranyloxy)-1-(2-imino-1,2-dihydro-1-pyridyl)-2-propanol |
| 3475 | 3-(2-acetyl-7-benzofuranyloxy)-1,2-epoxypropane | 2-aminopyridine | 3-(2-acetyl-7-benzofuranyloxy)-1-(2-imino-1,2-dihydro-1-pyridyl)-2-propanol |
| 3486 | 3-(7-benzothienyloxy)-1,2-epoxy-propane | 2-aminopyridine | 3-(7-benzothienyloxy)-1-(2-imino-1,2-dihydro-1-pyridyl)-2-propanol |
| 3439 | 3-(8-coumarinyloxy)-1,2-epoxy-propane | 2-aminopyridine | 3-(8-coumarinyloxy)-1-(2-imino-1,2-dihydro-1-pyridyl)-2-propanol |
| 3446 | 3-(5-methyl-8-coumarinyloxy)-1,2-epoxypropane | 2-aminopyridine | 3-(5-methyl-8-coumarinyloxy)-1-(2-imino-1,2-dihydro-1-pyridyl)-2-propanol |
| 3483 | 3-(8-thiochromanyloxy)-1,2-epoxyproane | 2-aminopyridine | 3-(8-thiochromanyloxy)-1-(2-imino-1,2-dihydro-1-pyridyl)-2-propanol |
| 3496 | 3-(5-quinolyloxy)-1,2-epoxy-propane | 2-aminopyridine | 3-(5-quinolyloxy)-1-(2-imino-1,2-dihydro-1-pyridyl)-2-propanol |
| 3489 | 3-(1-naphthoxy)-1,2-epoxypropane | 2-amino-3-acetoxypyridine | 3-(1-naphthoxy)-1-(2-imino-3-acetoxy-1,2-dihydro-1-pyridyl)-2-propanol |
| 3455 | 3-(1-naphthoxy)-1,2-epoxypropane | 2-amino-3-acetmidopyridine | 3-(1-naphthoxy)-1-(2-imino-3-acetamido-1,2-dihydro-1-pyridyl)-2-propanol |
| 3459 | 3-(1-naphthoxy)-1,2-epoxypropane | 2-amino-3-nitropyridine | 3-(1-naphthoxy)-1-(2-imino-3-nitro-1,2-dihydro-1-pyridyl)-2-propanol |
| 3485 | 3-(1-naphthoxy)-1,2-epoxypropane | 2-amino-4,6-dimethylpyridine | 3-(1-naphthoxy)-1-(2-imino-4,6-dimethyl-1,2-dihydro-1-pyridyl)-2-propanol |
| 4394 | 3-(1-naphthoxy)-1,2-epoxypropane | 2-amino-3,5-dichloropyridine | 3-(1-napnthoxy)-1-(2-imino-3,5-dichloro-1,2-dihydro-1-pyridyl)-2-propanol |
| 4335 | 3-(1-naphthoxy)-1,2-epoxypropane | 2-amino-3-hydroxypyridine | 3-(1-naphthoxy)-1-(2-imino-3-hydroxy-1,2-dihydro-1-pyridyl)-2-propanol |
| 3465 | 3-(1-naphthoxy)-1,2-epoxypropane | 2-amino-3-methoxypyridine | 3-(1-naphthoxy)-1-(2-imino-3-methoxy-1,2-dihydro-1-pyridyl)-2-propanol |
| 4370 | 3-(1-naphthoxy)-1,2-epoxypropane | 2,6-diaminopyridine | 3-(1-naphthoxy)-1-(2-imino-6-amino-1,2-dihydro-1-pyridyl)-2-propanol |
| 3490 | 3-(1-naphthoxy)-1,2-epoxypropane | 2-amino-3-hydroxymethyl-pyridine | 3-(1-naphthoxy)-1-(2-imino-3-hydroxymethyl-1,2-dihydro-1-pyridyl)-2-propanol |
| 3443 | 3-(1-naphthoxy)-1,2-epoxypropane | 2-allylaminopyridine | 3-(1-naphthoxy)-1-(2-allylimino-1,2-dihydro-1-pyridyl)-2-propanol |
| 3424 | 3-(1-naphthoxy)-1,2-epoxypropane | 2-phenylaminopyridine | 3-(1-naphthoxy)-1-(2-phenylimino-1,2-dihydro-1-pyridyl)-2-propanol |
| 3436 | 3-(1-naphthoxy)-1,2-epoxypropane | 2-benzylamiopyridine | 3-(1-naphthoxy)-1-(2-benzylimino-1,2-dihydro-1-pyridyl)-2-propanol |
| 3416 | 3-(1-naphthoxy)-1,2-epoxypropane | 2-cyclohexylaminopyridine | 3-(1-naphthoxy)-1-(2-cyclohexylimino-1,2-dihydro-1-pyridyl)-2-propanol |
| 4528 | 3-(2-phenylphenoxy)-1,2-epoxy-propane | 2-aminopyridine | 3-(2-phenylphenoxy)-1-(2-imino-1,2-dihydro-1-pyridyl)-2-propanol |

TABLE I-continued

| COMPOUND # | REAGENTS | | PRODUCT |
|---|---|---|---|
| 4568 | 3-(1-naphthoxy)-1,2-epoxypropane | 3-ethoxy-2-aminopyridine | 3-(1-naphthoxy)-1-(2-imino-3-ethoxy-1,2-dihydro-1-pyridyl)-2-propanol |

EXAMPLE IV

This example illustrates the synthesis of 3-(1-naphthoxy)-1-(2-methoxycarbonylimino-1,2-dihydro-1-pyridyl)-2-methoxycarbonyloxypropane, a bis(methoxycarbonyl) derivative of the compound of Example II.

A solution of 4.4 grams (0.15 millimoles) of the compound of Example II in benzene and 50 ml of saturated sodium carbonate solution were placed in a flask and stirred vigorously. Then 3.1 grams (2.2 equivalents) of methylchloroformate in 5 ml of benzene were added dropwise. The compound of Example II was first in suspension and subsequently went into solution and a precipitate appeared. The benzene solution was separated and the precipitate in the aqueous phase was collected by filtration, washed with water, and recrystallized twice from acetone. White crystals were obtained, M.P. 161°–164° C. (dec.).

EXAMPLE V

By the procedure of Example IV, using the reagents listed in Table II, the product compounds listed in the table are obtained.

TABLE II

| COMPOUND # | REAGENTS | | PRODUCT |
|---|---|---|---|
| 4540 | 3-(1-naphthoxy)-1-(2-imino-1,2-dihydro-1-pyridyl)-2-propanol | propionyl chloride | 3-(1-naphthoxy)-1-(2-propionylimino-1,2-dihydro-1-pyridyl)-2-propionyloxypropane |
| 3498 | 3-(1-naphthoxy)-1-(2-imino-1,2-dihydro-1-pyridyl)-2-propanol | carbamoyl chloride | 3-(1-naphthoxy)-1-(2-carbamoylimino-1,2-dihydro-1-pyridyl)-2-carbamyloxypropane |
| 3469 | 3-(1-naphthoxy)-1-(2-imino-1,2-dihydro-1-pyridyl)-2-propanol | thiocarbamoyl chloride | 3-(1-naphthoxy)-1-(2-thiocarbamoylimino-1,2-dihydro-1-pyridyl)-2-thiocarbamyloxypropane |

EXAMPLE VI 3-(1-Naphthoxy)-1-(2-imino-1,2-dihydro-1-pyridyl)-2-propanol, O-hemisuccinate ester.

7.0 Grams (0.024 mole) of 3-(1-naphthoxy)-1-(2-imino-1,2-dihydro-1-pyridyl)-2-propanol and 2.62 grams (1.1 equivalents, 0.026 mole) of succinic anhydride were added to 175 milliliters of tetrahydrofuran and the heterogeneous mixture was stirred at room temperature overnight for 3 days. The precipitate which formed was collected on a filter, washed with tetrahydrofuran and diethyl ether, and dried. M.P. 154°–156° C.

EXAMPLE VII

Following the procedure of Example VI the reagents listed in Table III are reacted to produce the compounds of this invention listed in the table.

EXAMPLE VIII

This example illustrates the formation of an acid addition compound according to this invention.

18 Grams of 3-(1-naphthoxy)-1-(2-methoxycarbonylimino-1,2-dihydro-1-pyridyl)-2-methoxycarbonyloxypropane were dissolved in about 50 ml of absolute ethanol. Concentrated hydrochloric acid was added dropwise until the pH was 1.0. The mixture was heated until a homogeneous solution was obtained and additional hydrochloric acid was added to bring the pH to 1.0. The solvent was evaporated under vacuum and the residual oil was dissolved in 25 milliliters of hot isopropyl alcohol. The product which crystallized on cooling was collected on a filter, washed with isopropyl alcohol, and dried to yield 3-(1-naphthoxy)-1-(2-chloro-2-methoxycarbonylamino-1,2-dihydro-1-pyridyl)-2-methoxycarbonyloxypropane. M.P. 133°–135° C.

We claim:

1. A compound having the structural formula:

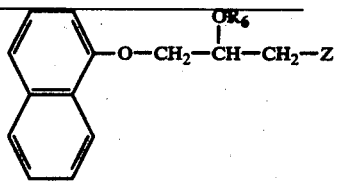

wherein: Z is an iminopyridyl radical having the structural formula

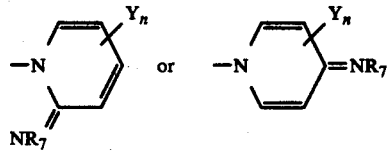

wherein: Y is selected from the group consisting of hydrogen, loweralkyl, loweralkenyl, loweralkoxy, loweralkoxycarbonyl, loweracyloxy, loweracylamino, carbamoyl, cyano, halo, and n = 1 or 2 when Y is loweralkyl or halo, and n = 1 in all other cases; $R_6$ is se-

TABLE III

| COMPOUND # | REAGENTS | | PRODUCT |
|---|---|---|---|
| 4466 | 3-(1-naphthoxy)-1-(2-imino-1,2-dihydro-1-pyridyl)-2-propanol | maleic anhydride | 3-(1-naphthoxy)-1-(2-imino-1,2-dihydro-1-pyridyl)-2-propanol, O-hemimaleate ester |
| 4470 | 3-(1-naphthoxy)-1-(2-imino-1,2-dihydro-1-pyridyl)-2-propanol | glutaric anhydride | 3-(1-naphthoxy)-1-(2-imino-1,2-dihydro-1-pyridyl)-2-propanol, O-hemiglutarate ester | lected from the group consisting of hydrogen, loweralkoxycarbonyl, loweracyl, carboxyloweracyl, carbamoyl, thiocarbamoyl and $R_7$ is selected from the group consisting of hydrogen, loweralkyl, loweralkenyl, loweralkynyl, $C_3$-$C_6$ cycloalkyl, $C_4$-$C_8$ cycloalkylalkyl, phenyl, benzyl, phenylethyl, loweralkoxycarbonyl, loweracyl, carboxyloweracyl, carbamoyl, thiocarbamoyl; and pharmaceutically acceptable acid addition compounds.

2. 3-(1-Naphthoxy)-1-(2-imino-1,2-dihydro-1-pyridyl)-2-propanol and pharmaceutically acceptable acid addition compounds.

3. 3-(1-Naphthoxy)-1-(2-methoxycarbonylimino-1,2-dihydro-1-pyridyl)-2-methoxycarbonyloxypropane and pharmaceutically acceptable acid addition compounds.

4. 3-(1-Naphthoxy)-1-(2-imino-1,2-dihydro-1-pyridyl)-2-propanol, O-hemisuccinate ester and pharmaceutically acceptable acid addition compounds.

5. 3-(1-Naphthoxy)-1-(2-imino-1,2-dihydro-3-methyl-1-pyridyl)-2-propanol and pharmaceutically acceptable acid addition compounds.

6. 3-(4-Indanyloxy)-1-(2-imino-1,2-dihydro-1-pyridyl)-2-propanol and pharmaceutically acceptable acid addition compounds.

7. 3-(5-Indanyloxy)-1-(2-imino-1,2-dihydro-1-pyridyl)-2-propanol and pharmaceutically acceptable acid addition compounds.

8. 3-(1-Naphthoxy)-1-(2-propionylimino-1,2-dihydro-1-pyridyl)-2-propionyloxypropane and pharmaceutically acceptable acid addition compounds.

9. 3-(1-Naphthoxy)-1-(4-imino-1,4-dihydro-1-pyridyl)-2-propanol and pharmaceutically acceptable acid addition compounds.

* * * * *